United States Patent [19]

Hsu

[11] Patent Number: 5,294,614

[45] Date of Patent: * Mar. 15, 1994

[54] SYNERGISTIC MICROBICIDAL COMPOSITION COMPRISING 3-ISOTHIAZOLONES AND 1-METHYL-3,5,7-TRIAZA-1-AZONIATRICYCLO(3.3.1.1)DECANE CHLORIDE

[75] Inventor: Jemin C. Hsu, Fort Washington, Pa.

[73] Assignee: Rohm and Haas Company, Philadelphia, Pa.

[*] Notice: The portion of the term of this patent subsequent to Mar. 2, 2010 has been disclaimed.

[21] Appl. No.: 3,712

[22] Filed: Jan. 13, 1993

[51] Int. Cl.$^5$ .................... A61K 31/53; A61K 31/425
[52] U.S. Cl. ..................................... 514/244; 514/372
[58] Field of Search .............................. 514/244, 372

[56] References Cited

U.S. PATENT DOCUMENTS

| | | | |
|---|---|---|---|
| 3,761,488 | 9/1973 | Lewis et al. | 260/302 |
| 4,105,431 | 8/1978 | Lewis et al. | 548/213 |
| 4,252,694 | 2/1981 | Lewis et al. | 252/545 |
| 4,265,899 | 5/1981 | Lewis et al. | 424/270 |
| 4,279,762 | 7/1981 | Lewis et al. | 252/47.5 |
| 4,650,866 | 3/1987 | Rayudu | 544/186 |
| 5,190,944 | 3/1993 | Hsu | 514/244 |

OTHER PUBLICATIONS

Willingham, *Chemical Abstracts:* 115(23):250362v, 1991.
Mixtures of Quaternary Ammonium Compounds and Long-chain Fatty Acids as Antifungal Agents, F. C. Kull, P. C. Eisman, H. D. Sylwestrowicz and R. L. Mayer, 1961, vol. 9, pp. 538-541.

*Primary Examiner*—Frederick E. Waddell
*Assistant Examiner*—William R. A. Jarvis
*Attorney, Agent, or Firm*—Michael B. Fein

[57] ABSTRACT

Microbicidal compositions comprising one or more 3-isothiazolones and 1-methyl-3,5,7-triaza-1-azoniatricyclo(3.3.1.1)decane chloride in synergistic amounts, methods, and articles are disclosed.

5 Claims, No Drawings

SYNERGISTIC MICROBICIDAL COMPOSITION COMPRISING 3-ISOTHIAZOLONES AND 1-METHYL-3,5,7-TRIAZA-1-AZONIATRICYCLO(3.3.1.1)DECANE CHLORIDE

BACKGROUND OF THE INVENTION

A. Field of the Invention

This invention concerns microbicidal compositions which are used as bactericides, fungicides and algaecides to eliminate, inhibit and/or prevent the growth of microbial organisms such as bacteria, fungi, and algae in various systems and products.

B. Prior Art

The 3-isothiazolones described in U.S. Pat. Nos. 3,761,488; 4,105,431; 4,252,694; 4,265,899; and 4,279,762 are known to have excellent microbicidal activity. Two important commercially available 3-isothiazolones are 2-n-octyl-3-isothiazolone, and a mixture of 5-chloro-2-methyl-3-isothiazolone and 2-methyl-3-isothiazolone.

1-Methyl-3,5,7-triaza-1-azoniatricyclodecane chloride is a known microbicide according to U.S. Pat. No. 4,650,866.

Combinations of certain microbicides, some of which exhibit synergy together, are known. However, several of such combinations exhibit disadvantages, either due to toxicity, cost, compatibility, or due to other problems.

It is the principal object of this invention to provide a microbicidal composition which is more efficacious than known microbicidal compositions, and overcomes other disadvantages of the prior art combinations.

SUMMARY OF THE INVENTION

These objects, and others as will become apparent from the following disclosure, are achieved by the present invention which comprises, in part, compositions comprising 1-methyl-3,5,7-triaza-1-azoniatricyclo(3.3.1.1)decane chloride and a 3-isothiazolone selected from the group consisting of 2-n-octyl-3-isothiazolone, 5-chloro-2-methyl-3-isothiazolone, 2-methyl-3-isothiazolone, and mixtures of two or more thereof.

The invention also comprises a method of inhibiting or preventing the growth of bacteria, fungi, or algae in a locus subject or susceptible to contamination thereby which comprises incorporating said composition into or onto said locus in an amount effective to inhibit or prevent said growth.

DETAILED DESCRIPTION OF THE INVENTION AND THE PREFERRED EMBODIMENTS

Important applications of the synergistic antimicrobial compositions of the present invention include, but are not limited to: inhibiting the growth of bacteria and fungi in aqueous paints a coatings, adhesives, sealants, latex emulsions, and joint cements; preserving wood; preserving cutting fluids; controlling slime-producing bacteria and fungi in pulp and papermills and cooling towers; as a spray or dip treatment for textiles and leather to prevent mold growth; protecting paint films, especially exterior paints, from fungal attack which occurs during weathering of the paint film; protecting processing equipment from slime deposits during manufacture of cane and beet sugar; preventing microorganism buildup and deposits in air washer or scrubber systems and in industrial fresh water supply systems; preserving fuel; controlling microorganism contamination and deposits in oil field drilling fluids and muds, and in secondary petroleum recovery processes; preventing bacterial and fungal growth in paper coatings and coating processes; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types; as a hard surface disinfectant to prevent growth of bacteria and fungi on walls, floors, etc.; as a preservative for cosmetic and toiletry raw materials, floor polishes, fabric softeners, household and industrial cleaners; in swimming pools to prevent algae growth; inhibiting the growth of harmful bacteria, yeasts, fungi on plants, trees, fruits, seeds, or soil; preserving agricultural formulations, electrodeposition systems, diagnostic and reagent products, medical devices; protecting animal dip compositions against the buildup of microorganisms; in photoprocessing to prevent buildup of microorganisms, and the like.

The components of the compositions of the invention may be added separately to any system or may be formulated as a simple mixture comprising its essential ingredients, and if desired, a suitable carrier or solvent, or as an aqueous emulsion or dispersion.

The compositions of the invention have unexpectedly enhanced antimicrobial activity against a wide range of microorganisms. As a result of the synergy, the effective dose required can be lowered, which is not only more economical but also increases safety margins. The synergistic compositions of the present invention provide more effective and broader control of microorganisms in a number of systems.

The present invention thus provides a composition having microbicidal activity which includes a 3-isothiazolone, selected from the group consisting of 2-n-octyl-3-isothiazolone ("893") and a 3:1 mixture of 5-chloro-2-methyl-3-isothiazolone and 2-methyl-3-isothiazolone ("886"), as a first component and 1-methyl-3,5,7-triaza-1-azoniatricyclo(3.3.1.1)decane chloride ("Busan 1024" or "1024∞") as a second component wherein the weight ratio of the first component to the second component is from about 1:2 to about 1:18000.

The composition of the invention can be formulated as a solution in a wide range of solvents. The solutions may contain from about 0.1 to 99.9%; preferably from about 5 to 30% by weight, of the active composition. It is generally more convenient to provide the compositions in a water-dilutable form. This may be accomplished by adding an emulsifier to the organic solution followed by dilution with water. In formulating the solutions, organic solvents such as ethanol, propanol, isopropanol, diethylene glycol, dipropylene glycol, polyethylene glycol, ethyl ether, and the like, may be employed. Various other conventional additives may be employed, such as surfactants, dispersing agents, corrosion inhibitors, and the like.

The following specific examples are presented to illustrate certain embodiments of the present invention but are not to be construed as limitations thereof. All percentages are by weight unless otherwise specified.

EXAMPLES

The synergism of two-component compositions is demonstrated by testing a wide range of concentrations and ratios of compounds, generated by two-fold serial dilutions in a Trypticase Soy Broth (TSB) growth medium of a microbicide in one dimension and another microbicide in the second dimension, against a bacterium Escherichia coli (ATCC 11229) and a fungus Rhodotorula rubra. Each test tube was inoculated to make about $1-5\times10^7$ bacteria per ml or $1-5\times10^5$ fungi per ml. The lowest concentrations of each compound or mixtures to inhibit visible growth (turbidity) at 37° C. for E. coli and at 30° C., for R. rubra were taken as the minimum inhibitory concentration (MIC). The MICs were taken as end points of activity. End points for the mixtures of compound A (3-isothiazolone) and compound B (1-methyl-3,5,7-triaza-1-azoniatricyclo(3.3.1.1)decane chloride) were then compared with the end points for the isothiazolone A and compound B alone. Synergism was determined by a commonly used and accepted method described by Krull, F. C.; Eisman, P. C.; Sylwestrowicz, H. D.; and Mayer, R. L., in Applied Microbiology, vol. 9, pp 538–541 (1961) using the ratio determined by $Qa/QA + Qb/QB =$ Synergy Index (SI)

wherein

QA = concentration of compound A in parts per million (ppm), acting alone, which produced an end point;

Qa = concentration of compound A in ppm, in the mixture, which produced an end point;

QB = concentration of compound B in ppm, acting alone, which produced an end point;

Qb = concentration of compound B in ppm, in the mixture, which produced an end point.

When the sum of Qa/QA and Qb/QB is greater than one, antagonism is indicated. When the sum is equal to one, additivity is indicated, and when the sum is less than one, synergism is demonstrated.

The test results for demonstration of synergism of microbicide combinations are shown in Tables 1 and 2. Each table concerns the combination of 1-methyl-3,5,7-triaza-1-azoniatricyclo(3.3.1.1)decane chloride and an isothiazolone, and shows:

1. the identity of the isothiazolone (compound A);
2. test against E. coli and R. rubra;
3. the end point activity in ppm measured by MIC for compound A alone (QA), for compound B alone (QB), for compound A in the mixture (Qa), and for compound B in the mixture (Qb);
4. the calculation of the synergy index (SI) based on the formula described above, and the weight ratio of compound A to 1-methyl-3,5,7-triaza-1-azoniatricyclo(3.3.1.1)decane chloride in the particular combination (A:B);
5. the range of weight ratios for synergism and the preferred weight ratios. It will be appreciated by those skilled in the art that the ratios given are approximate.

The MIC values of each compound tested alone (QA or QB) are end point activities and are also reported in Tables 1 and 2.

TABLE 1

| 886(Compound A)/1024(Compound B) Combination | | | |
|---|---|---|---|
| A | B | A:B | Synergy Index |
| Tested in TSB with Escherichia coli | | | |
| 8 ppm | 0 ppm | | |
| 4 | 35 | 1:8.7 | 0.53 |
| 4 | 70 | 1:17.5 | 0.56 |

TABLE 1-continued

| 886(Compound A)/1024(Compound B) Combination | | | |
|---|---|---|---|
| A | B | A:B | Synergy Index |
| 4 | 140 | 1:35 | 0.62 |
| 4 | 280 | 1:70 | 0.75 |
| 2 | 562 | 1:281 | 0.75 |
| 1 | 562 | 1:562 | 0.62 |
| 0.5 | 562 | 1:1124 | 0.56 |
| 0 | 1125 | | |
| Tested in TSB with Rhodotorula rubra | | | |
| 4 ppm | 0 ppm | | |
| 2 | 70 | 1:35 | 0.51 |
| 2 | 140 | 1:70 | 0.52 |
| 1 | 140 | 1:140 | 0.27 |
| 1 | 281 | 1:281 | 0.28 |
| 1 | 562 | 1:562 | 0.31 |
| 1 | 1125 | 1:1125 | 0.37 |
| 0.5 | 1125 | 1:2250 | 0.24 |
| 0.5 | 2250 | 1:4500 | 0.37 |
| 0.5 | 4500 | 1:9000 | 0.62 |
| 0.25 | 4500 | 1:18000 | 0.56 |
| 0 | 9000 | | |

TABLE 2

| 893(Compound A)/1024(Compound B) Combination | | | |
|---|---|---|---|
| A | B | A:B | Synergy Index |
| Tested in TSB with Escherichia coli | | | |
| 32 ppm | 0 ppm | | |
| 8 | 562 | 1:70 | 0.75 |
| 4 | 562 | 1:140 | 0.62 |
| 2 | 562 | 1:281 | 0.56 |
| 0 | 1125 | | |
| Tested in TSB with Rhodotorula rubra | | | |
| 8 ppm | 0 ppm | | |
| 4 | 8 | 1:2 | 0.50 |
| 4 | 16 | 1:4 | 0.50 |
| 4 | 31 | 1:8 | 0.51 |
| 4 | 62 | 1:16 | 0.51 |
| 4 | 125 | 1:32 | 0.52 |
| 4 | 250 | 1:62 | 0.53 |
| 4 | 500 | 1:125 | 0.56 |
| 4 | 1000 | 1:250 | 0.62 |
| 4 | 2000 | 1:500 | 0.75 |
| 2 | 4000 | 1:2000 | 0.75 |
| 0 | 8000 | | |

The data in Tables 1 and 2 demonstrate synergistic antimicrobial activities and show surprisingly greater activity than the algebraic sum of individual ingredients which make up the respective composition. The synergistic activities of the compositions of the invention in most cases are applicable to bacteria, fungi, and a mixture of bacteria and fungi. Thus, the combinations not only lower the use-level of biocide, but also broaden the spectrum of activity. This is especially useful in situations where either component alone does not achieve the best results due to weak activity against certain organisms.

While this invention has been described in sufficient detail for those skilled in the art to be able to make and use it, various alternatives, modifications, and improvements should become apparent from the foregoing disclosure without departing from the spirit and scope of the invention.

What is claimed is:

1. A synergistic microbicidal composition comprising 1-methyl-3,5,7-triaza-1-azoniatricyclo(3.3.1.1)decane chloride and a 3-isothiazolone compound selected from the group consisting of 2-n-octyl-3-isothiazolone, 5-chloro-2-methyl-3-isothiazolone, 2-methyl-3-isothiazolone, and mixtures of two or more thereof; in a weight ratio of about 1:2 to about 1:2000.

2. The composition of claim 1 wherein said 3-isothiazolone is an approximate 3:1 by weight mixture of 5-chloro-2-methyl-3-isothiazolone to said 1-methyl-3,5,7-triaza-1-azoniatricyclo(3.3.1.1)decane chloride is from about 1:87 to about 1:2000.

3. A method for inhibiting the growth of bacteria or fungi in a locus subject to contamination thereof comprising incorporating at, onto, or into the locus, in an amount which is effective to adversely affect the growth of bacteria or fungi, the composition of claim 1.

4. The method according to claim 3 wherein said locus is an aqueous medium.

5. The composition according to claim 1 wherein said composition additionally contains an emulsifier and water.

* * * * *

UNITED STATES PATENT AND TRADEMARK OFFICE
CERTIFICATE OF CORRECTION

PATENT NO. : 5,294,614

DATED : March 15, 1994

INVENTOR(S) : Jemin C. Hsu

It is certified that error appears in the above-identified patent and that said Letters Patent is hereby corrected as shown below:

Column 1, line 56 change "a coatings" to read -- and coatings --

Column 2, line 48 change "0.1" to read -- 0.01 --

Column 5, line 5 change "1:87" to read -- 1:8.7 --

Signed and Sealed this

Twenty-fifth Day of October, 1994

Attest:

BRUCE LEHMAN

Attesting Officer

Commissioner of Patents and Trademarks